United States Patent
Gelman et al.

(10) Patent No.: US 8,474,338 B2
(45) Date of Patent: Jul. 2, 2013

(54) APPARATUS AND METHOD FOR ENGAGING ACOUSTIC VIBRATION SENSORS TO SKIN

(75) Inventors: Gregory Gelman, Rehovot (IL); Guy Ben-Ezra, Karkur (IL)

(73) Assignee: Deep Breeze Ltd., Orakiva (IL)

( * ) Notice: Subject to any disclaimer, the term of this patent is extended or adjusted under 35 U.S.C. 154(b) by 372 days.

(21) Appl. No.: 12/805,082

(22) Filed: Jul. 12, 2010

(65) Prior Publication Data

US 2011/0005320 A1    Jan. 13, 2011

Related U.S. Application Data

(60) Provisional application No. 61/224,947, filed on Jul. 13, 2009.

(51) Int. Cl.
*G01D 21/00* (2006.01)
*G01D 11/30* (2006.01)

(52) U.S. Cl.
CPC .................................... *G01D 11/30* (2013.01)
USPC ........................................................ 73/866.5

(58) Field of Classification Search
USPC .................. 600/528, 538, 533; 73/866.5, 529
See application file for complete search history.

(56) References Cited

U.S. PATENT DOCUMENTS

| | | | |
|---|---|---|---|
| 2002/0183642 A1* | 12/2002 | Murphy | 600/532 |
| 2003/0045806 A1* | 3/2003 | Brydon | 600/534 |
| 2004/0236239 A1* | 11/2004 | Murray et al. | 600/528 |
| 2009/0093687 A1* | 4/2009 | Telfort et al. | 600/300 |
| 2010/0256512 A1* | 10/2010 | Sullivan | 600/529 |

FOREIGN PATENT DOCUMENTS

WO    WO 2009083942 A1 *   7/2009

OTHER PUBLICATIONS

Kraman, "Comparison of lung sound transducers using a biacousitic transducer testing system", 2006, American Pphysiological Society, J Appl Physiol 101, 469-476.*

* cited by examiner

*Primary Examiner* — Peter Macchiarolo
*Assistant Examiner* — Tamiko Bellamy

(57) ABSTRACT

A system comprising a viscoelastic interface sheet to engage a sound vibrations sensors array to a sound generating objects. The structure of the interface sheet includes elements for easy handling, positioning and mounting. A device for storage and mounting support of such interface sheets is disclosed.

5 Claims, 10 Drawing Sheets

APPARATUS AND METHOD FOR ENGAGING ACOUSTIC VIBRATION SENSORS TO SKIN

CROSS-REFERENCE TO RELATED PATENT APPLICATIONS

This patent application claims priority from and is related to U.S. Provisional Patent Application Ser. No. 61/224,947, filed 13 Jul. 2009, this U.S. Provisional Patent Application incorporated by reference in its entirety herein.

FIELD OF THE INVENTION

The invention is related to the field of acoustic vibration monitoring and recording, and more particularly, to the engagement of acoustic vibration sensors to different objects, including human body skin for medical uses.

BACKGROUND OF THE INVENTION

Acoustical sensors are attached to objects generating sound in various ways. Simple stethoscopes are hand-held against the skin of the patient using hand-force of the physician.

The VRIxp, an acoustic vibrations recorder manufactured by Deep Breeze Ltd., Or Akiva, Israel, uses vacuum suction to attach and hold an array of sensors to human skin. This method has the following disadvantages:

- Issues with adhering to hairy skin due to vacuum leaks
- Limited duration in which the sensors can remain on the skin due to potential hematoma
- Requires a vacuum pump of a certain size and electrical needs in order to produce the required vacuum level.
- The vacuum pump creates noise during operation
- Leaks near the sensors location may create artificial noise which may affect the recorded sounds
- The vacuum system in whole is exposed to leaks which may reduce the adherence strength
- Detachment and re-attachment of sensors during the breathing cycle due to changes in vacuum levels may simulate false pathological sounds such as crackles (rales)
- The overall cost of a vacuum system is high
- The user is required to oversee that the vacuum system is in good performance during operation Other methods of adhering an array of sensors to the skin and having certain limitations may include:

- Utilization of body weight laying over the sensors toward gravity A belt or a vest which is wrapped around the patients and presses the sensors to the skin.

A main issue of acoustic transmission between sound vibration sensors (SVS) and sound generating object (SGO) is related to the passage of acoustic waves from the SGO to the SVS through an air layer. The difference in the three materials involved results in reflection and scatters of acoustic energy, causing loss of energy and echoes, resulting in poor acoustic detection quality. To overcome this problem, materials of the SVS are designed to have similar acoustic properties as the SGO. To overcome the air layer between the SGO and the SVS, an acoustic matching interface is commonly used. One such common example is ultrasound imaging in medical applications. The impedance matching material is a paste commonly known as ultrasound gel, such as Parker Aquasonic® 100 Ultrasound Transmission Gel, manufactured by Parker Laboratories, Inc. of Fairfield, N.J., USA. This gel replaces the air layer between the SGO and the SVS and reduces the acoustic reflection in the surfaces between the different materials.

These kinds of gel, provided in a form of paste, are inconvenient to use for three main reasons, explained in reference to the VRIxp:

1. The gel does not provide engagement characteristics to hold the SGO and the SVS together during the acoustic monitoring process. When using the VRIxp this creates a major inconvenience to the operator and might result in low quality accosting signal recording.

2. When the acoustic signal acquisition is completed, the gel needs to be wiped off the patient and the SVS. This causes inconvenience to the patient and additional work load to the operator of the RVIxp.

3. Remainders of gel might function as contamination carriers, carrying contamination from one patient to another. This requires disinfection of the SVS prior to usage with another patient, which creates yet additional load on the operator and still holds the risk of imperfect disinfection and cross-contamination.

It is the purpose of the present invention to provide methods and tools to improve the engagement of SVS to sound generating object, particularly to human tissue. These methods and tools provide considerable improvements for the three main issues associated with gel: (1) Engagement mechanism (2) Need for wiping off the gel (3) Risk of cross-contamination. The present invention also provides an efficient workflow for setting up acoustic monitoring.

SUMMARY OF THE INVENTION

In one embodiment of the present invention, an interface made of a soft layer of material is introduced between the SVS and the SGO. This interface is coated with glue on both sides, that adheres well to the surface of the soft material and provides lower adhesion force to the SVS and the SGO. This interface provides the acoustic matching interface by replacing the air gap between the SVS and the SGO, it provides the engagement mechanism through the glue coated surfaces, it requires no cleaning after use—it is simply peeled off the SGO and the SVS and it functions as a contamination barrier.

The invention will be described with reference to recording sounds from human respiratory activity, in medical use, using the VRIxp. This description is provided as an example and does not limit the scope of the invention to the described system and objects.

BRIEF DESCRIPTION OF THE DRAWINGS

The invention will be better understood in reference to the following Figures.

DETAILED DESCRIPTION OF THE INVENTION

Figure 1:
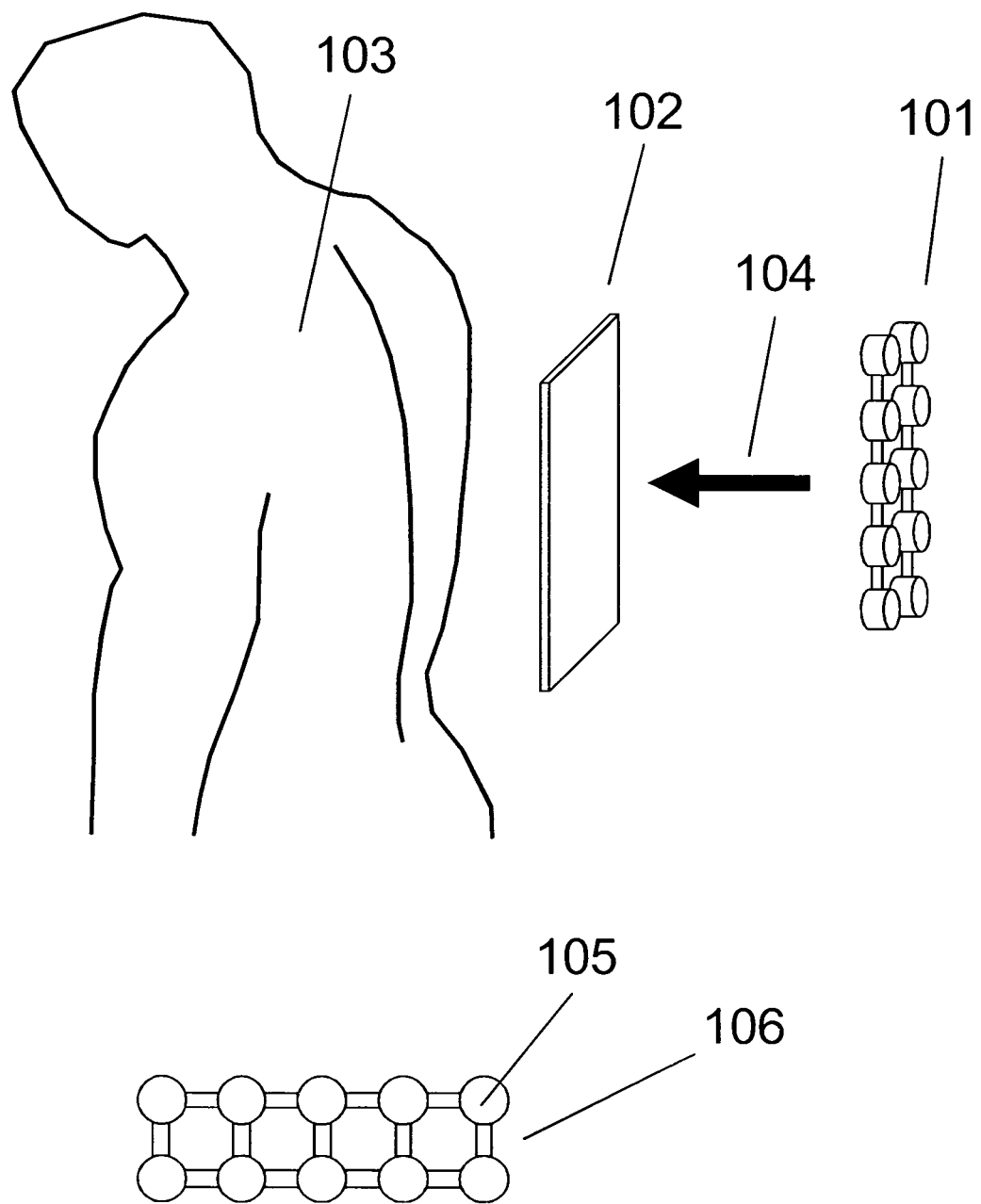
FIG. 1 is an illustration of the main elements involved in the present invention.

Reference is made now to FIG. 1, which is a general description of one embodiment of the system described in the context of the environment of respiration sounds recording from human patients, using the VRIxp. SVS array 101 is, for example, a set of 10 piezo-electric SVS units 105, arranged on a rectangular grid of 2×5 as shown by numerical reference 106. Such arrays, the way they are used, the connection to a computer and the complete environment are disclosed in details in the VRIxp product user manual, incorporated herein by reference, and on the website of Deep Breeze (www.deepbreze.com).

Interface 102 is a sheet of viscoelastic material coated with flexible adhesive material on both sides. The material is selected to provide low-stress displacement characteristics. One such example is No. 9880 3M Hydrogel Adhesive Tape distributed by 3M Health Care, St. Paul, Minn., USA. The layer of flexible adhesive material may further comprise an acoustic impedance matching layer.

Numerical reference 103 refers to an exposed human back ready for placement of the SVS array.

Figure 2:
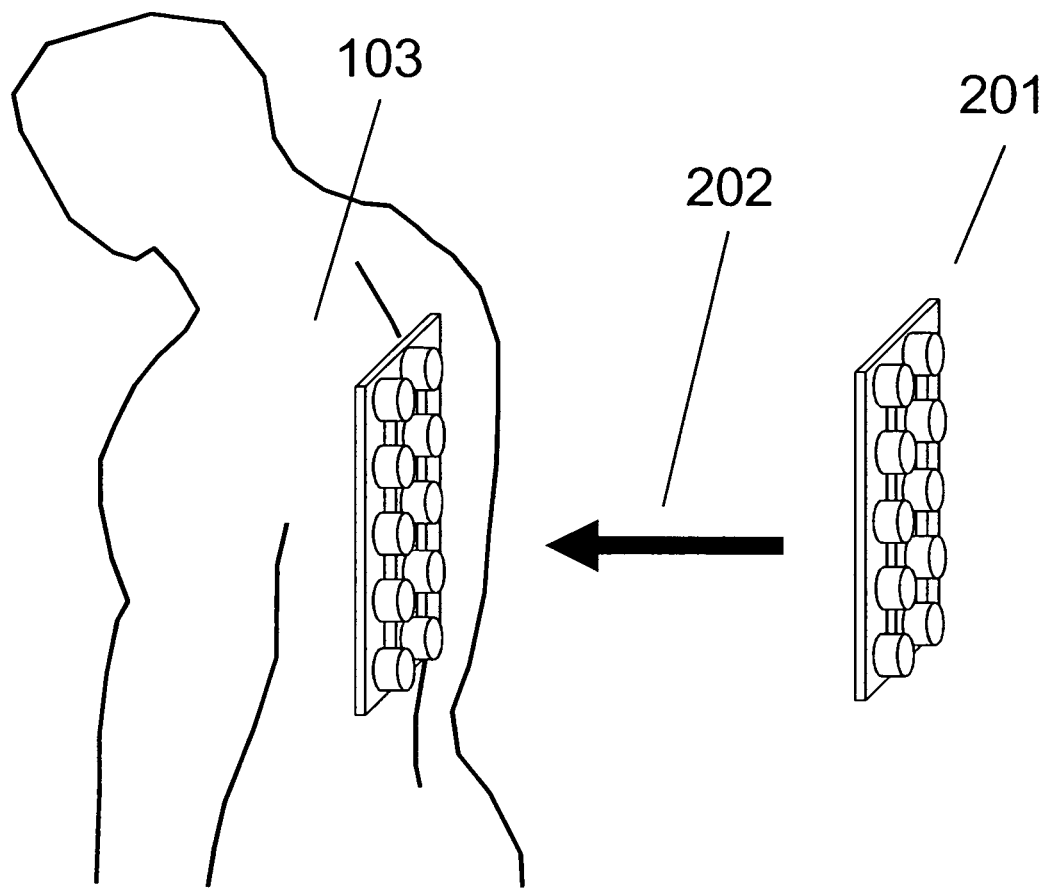
FIG. 2 illustrates a general mode of using the interface with the SVS for respiratory monitoring.

Placement of the SVS array is generally made in two steps. In the first step the SVS array 101 and the interface 102 are moved into contact (arrow 104) and pressed against each other to provide the assembly 201 of FIG. 2. With reference to FIG. 2, assembly 201 is moved now in direction 202 to be attached to the exposed back 103. This provides the complete assembly ready for respiratory acoustic monitoring. It would be appreciated that the order of placing the interface 102 on the SVS array 101 or the exposed back 103 is not limiting and can be reversed.

Figure 3:
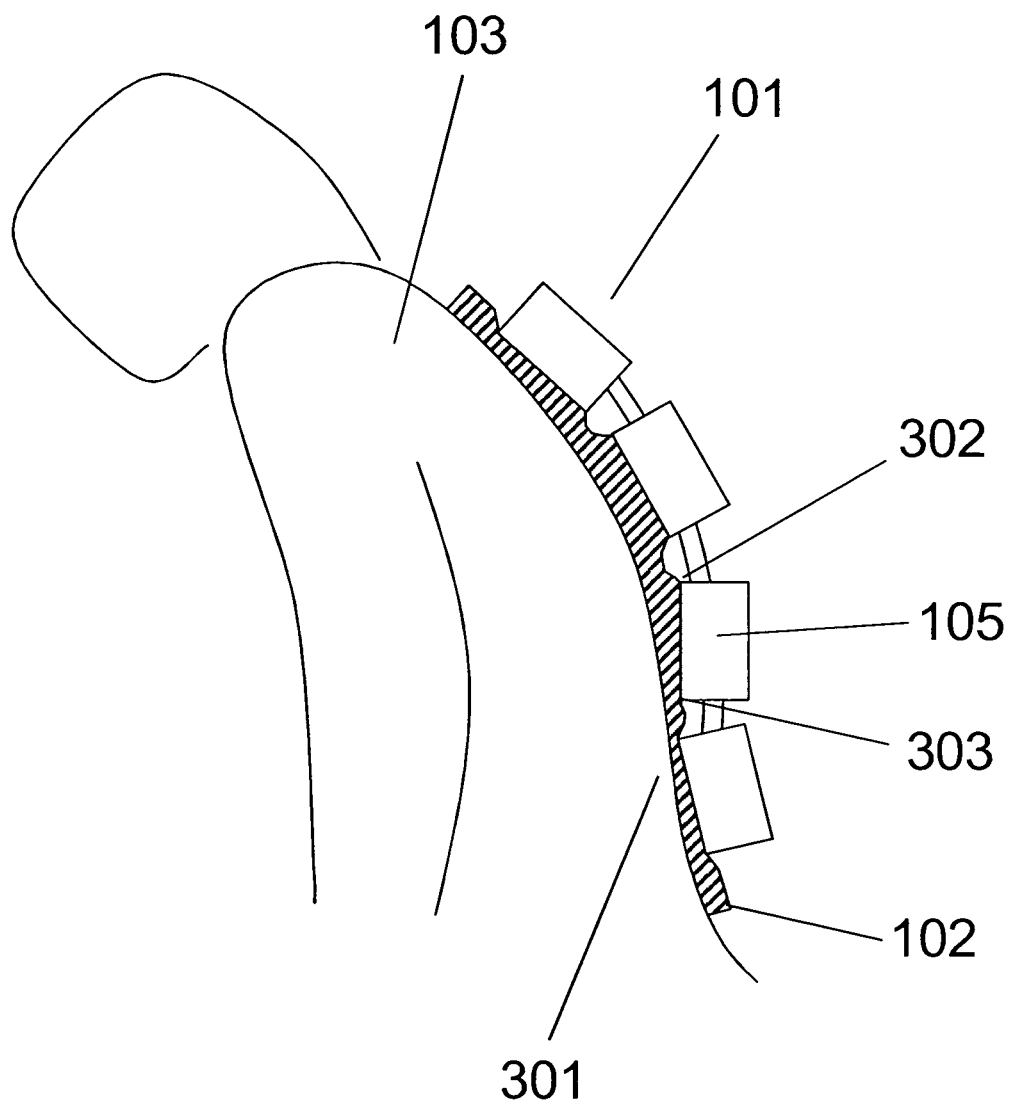
FIG. 3 demonstrates how the properties of the interface function to replace the air gap and provide the engagement force between the SVS and the patient.

Reference is made now to FIG. 3, which provides a side view of the complete assembly. Both the interface 102 and the SVS array 101 need to generally follow the exposed back curvature indicated by numerical reference 301. The SVS array 101 has a limited flexibility and each SVS 105 has flat surfaces. This prevents the SVS array 101 from completely follow the back curvature 301. As a result, considerable air gaps might be introduced between some of the SVS 105 and the exposed back surface 301, resulting in poor acoustic transmission.

Interface 102 is shown in FIG. 3 to be adhered to both SVS array 101 and exposed back surface 103. Also, the viscoelastic characteristics of the interface are shown where the interface easily gives way for low-stress increased thickness (302) and low-stress reduced thickness (303). This allows a relatively low adhesion glue to be able to hold the assembly in place, allows for relatively easy disassembly of the assembled SVS array 101, interface 102 and patient 103, and also enables efficient removal of air gaps between each SVS 105 and the exposed back 103.

Figure 4:
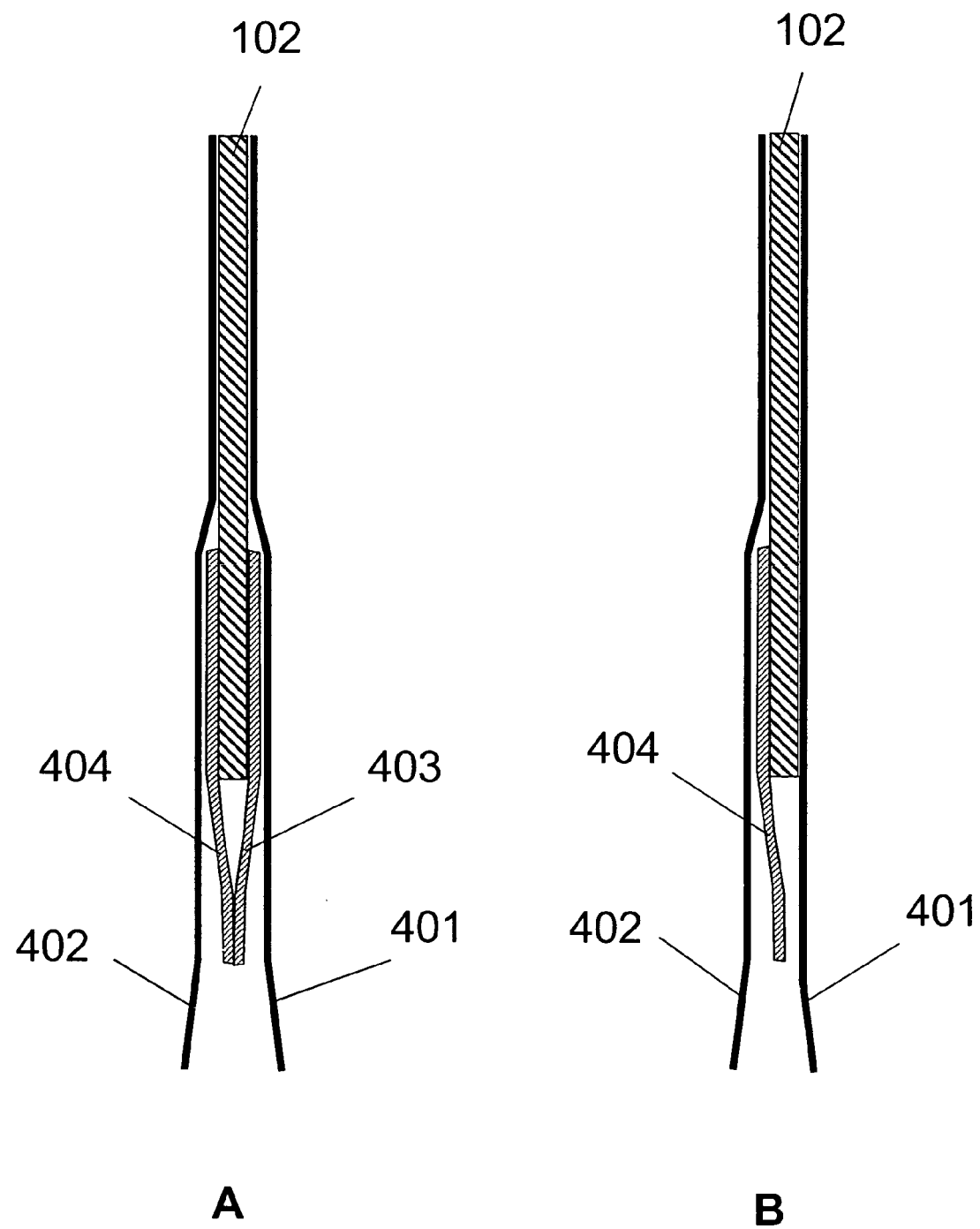
FIGS. 4A and 4B disclose two embodiments of the interface of the present invention.

Reference is made now to FIG. 4, disclosing another embodiment of the present invention.

In FIG. 4A interface 102 is shown with two liners 401 and 402 covering the whole area of the interface and optionally extending further if desired, typically up to 50 mm. Two separators 403 and 404 cover the whole width of the interface (perpendicular to the drawing surface) but only a fraction of its length, such as 10-20 mm from the edge and extend typically 0-30 mm from the edge of the interface. This is a configuration of the interface arranged for handling and storage prior to application to an SVS array. Liners 401 and 402 cover the glue coated surface of interface 102 to allow for holding by hand and placing on a table or a package without interfering with the glue on the interface surface. To mount the interface on an SVS array, the user first holds together liner 402 with separators 403 and 404 by one hand, and liner 401 by the other hand. By pulling the hands apart liner 401 is removed from the assembly of FIG. 4A and the glue layer of this side of the interface is exposed. The interface can now be attached to the SVS array with the exposed surface. In the next step the user holds together separators 403 and 404 and the SVS array by one hand and liner 402 by the other hand. The user can then peel-off liner 402 while interface 102 stays attached to the SVS array. The result is assembly 201 of FIG. 2, ready for placement on exposed back 103.

FIG. 4B discloses an embodiment similar to FIG. 4A except that separator 403 is not a part of the assembly. The mounting procedure of the embodiment of FIG. 4B is the same as the mounting procedure of FIG. 4A except for missing separator 403. In this embodiment, the single separator 404 might require improved strength contact to interface 102 since it experiences higher load than in the embodiment of FIG. 4A.

Liners 401 and 402 can be cut of different typical materials for such use. One such example is Rayoweb™ CR50, manufactured by Innovia Films Ltd. Tecumseh, Kans., USA.

Separators 403 and 404 can be cut of different typical materials for such use. One such example is plain paper.

Figure 5:
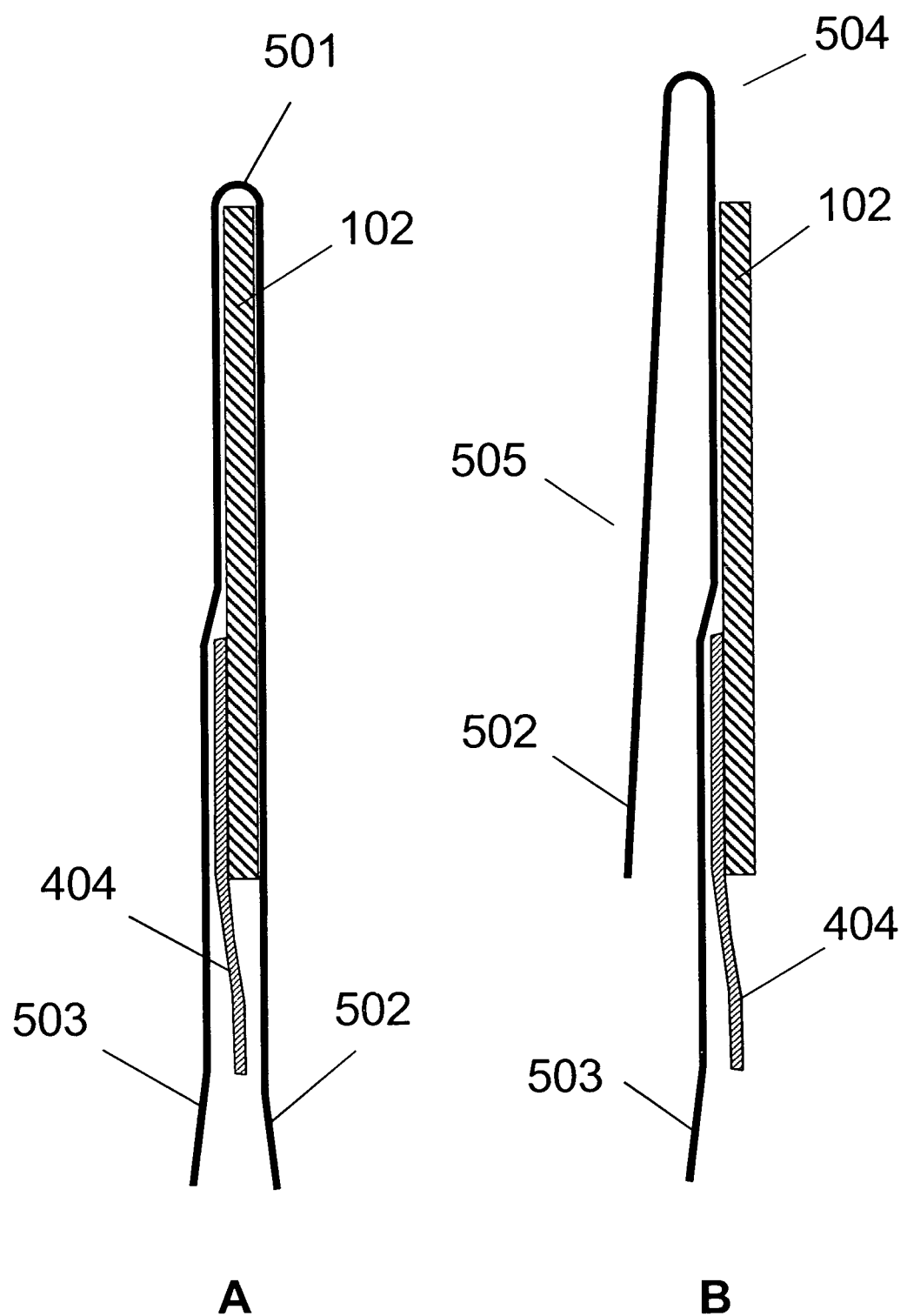
FIGS. 5A through 5B discloses an additional embodiment of the interface of the present invention.

Reference is made now to FIG. 5 disclosing an additional embodiment of the present invention. In FIG. 5A liners 401 and 402 of FIG. 4 are replaced by a single liner 501 covering interface 102 on both sides. The application of this embodiment onto the SVS array starts with holding together the left edge 503 of the liner together with separator 404 by one hand and holding the right edge 502 of the liner by the other hand. Then the right side of the liner is peeled off interface 102 and rotated anticlock wise to position 505 of FIG. 5B. The user can now hold the assembly without tampering with the glue surface by holding by one hand the lower part including liner edge 503 and separator 404 and by the other hand the top part 504 of the liner. The interface can now be applied to and pressed against the SVS array to provide assembly 201 of FIG. 2. To mount assembly 201 onto exposed back 103, liner 501 is removed by holding separator 404 against the SVS array by one hand and peeling-off the liner by the other hand, pulling away edge 503 of the liner.

Figure 6:
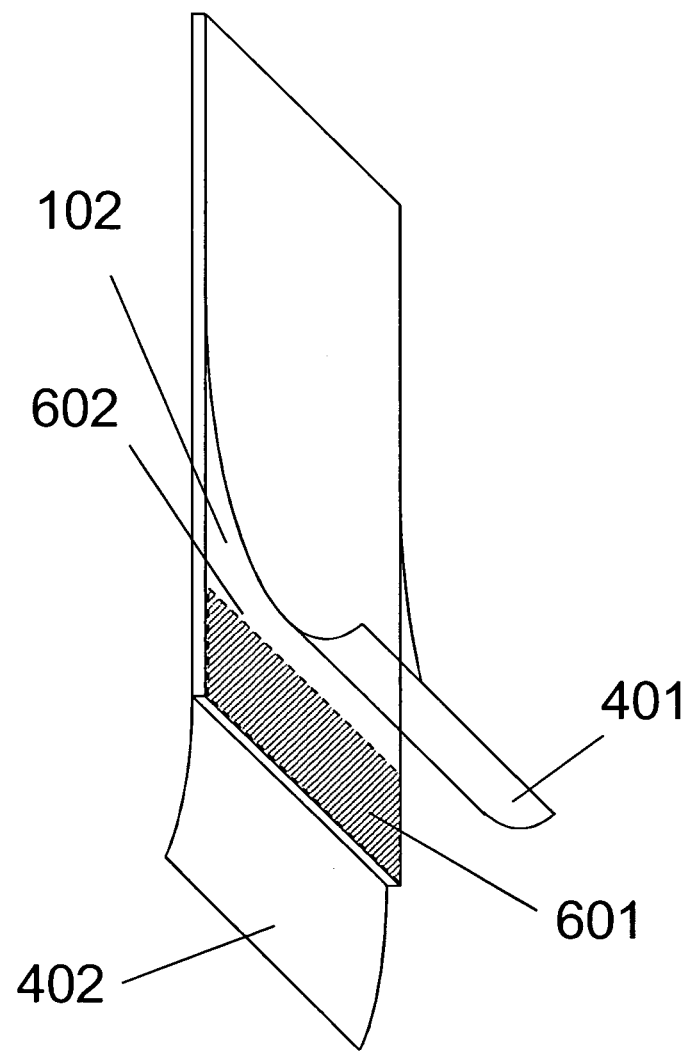
FIG. 6 discloses an additional embodiment of the interface of the present invention.

Reference is made now to FIG. 6, disclosing another embodiment of the invention. In this embodiment liner 401 is lifted from interface 102 to expose surface section 601 of the liner which is free of glue. This is another implementation of the function of separating liners 401 and 402. Since section 601 is clear of glue, it is very easy to separate it from liner 401. As such, section 601 and its parallel section on the other side of the interface (not shown) can assume the function of separators 403 and 404 in the procedure of mounting the interface on SVS array 101 and exposed back 103.

It will be appreciated by those skilled in the art that additional solutions are possible, such as coating section 601 with non-sticking paint over the glue, and that the specific description of the various embodiments does not limit the scope of the invention.

In addition, edge 602 of section 601 may be marked by various methods. One such method is printing a line on the liner or on the interface at the position of edge 602. Also usage of colored glue for the liner can be used to provide the user with a visual indication of edge 602. This indication will be used by the user for proper positioning of the interface on the SVS array, avoiding placement of area without glue onto the SVS array surface.

Figure 7:
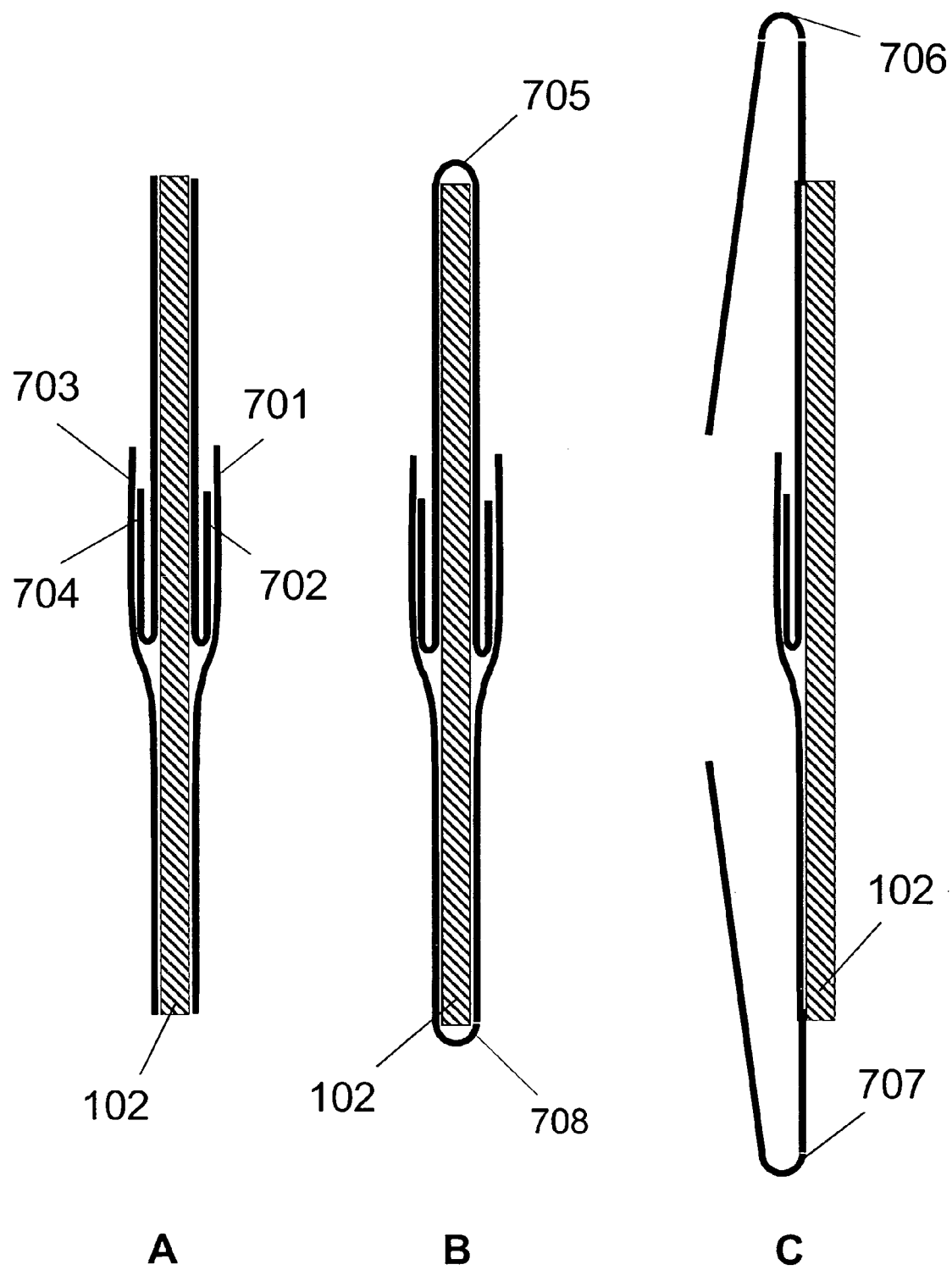
FIGS. 7A through 7C disclose an additional embodiment of the interface of the present invention.

Reference is made now to FIG. 7. In this embodiment of the invention separators are not required.

In FIG. 7a, two separate liners cover each side of interface 102. Liners 702, 704 are folded back onto themselves as shown, while liner 701, 703 overlaps liners 702, 704 respectively, typically extending 5-20 mm beyond the edge of the first liner.

The first step in applying the interface onto SVS array 101 is by holding the liner 701 generally where numerical reference 701 points at and lifting it. Then liner 702 is held generally where numerical reference 702 points at and lifted. Both liners 701 and 702 are removed from the interface, exposing the right glue surface ready to be mounted onto SVS array 102.

Liners 703 and 704 are removed using the same process of removing liners 701 and 702.

FIG. 7B discloses another configuration where liners 702 and 704 of FIG. 7A are made from a single liner 705, and similarly liners 701 and 703 are made from a single liner 708. With this configuration, when removing the liners from the right surface of the interface (in the same process of FIG. 7A), the liners are not detached from the assembly but are folded back to the left side as shown in FIG. 7C. At this stage the user can hold the assembly by the liner at the upper end 706 and by the liner at the lower end 707. This enables the attachment of the exposed right surface of the interface onto the SVS array 101 without tampering with the glue surface of interface 102.

Figure 8:
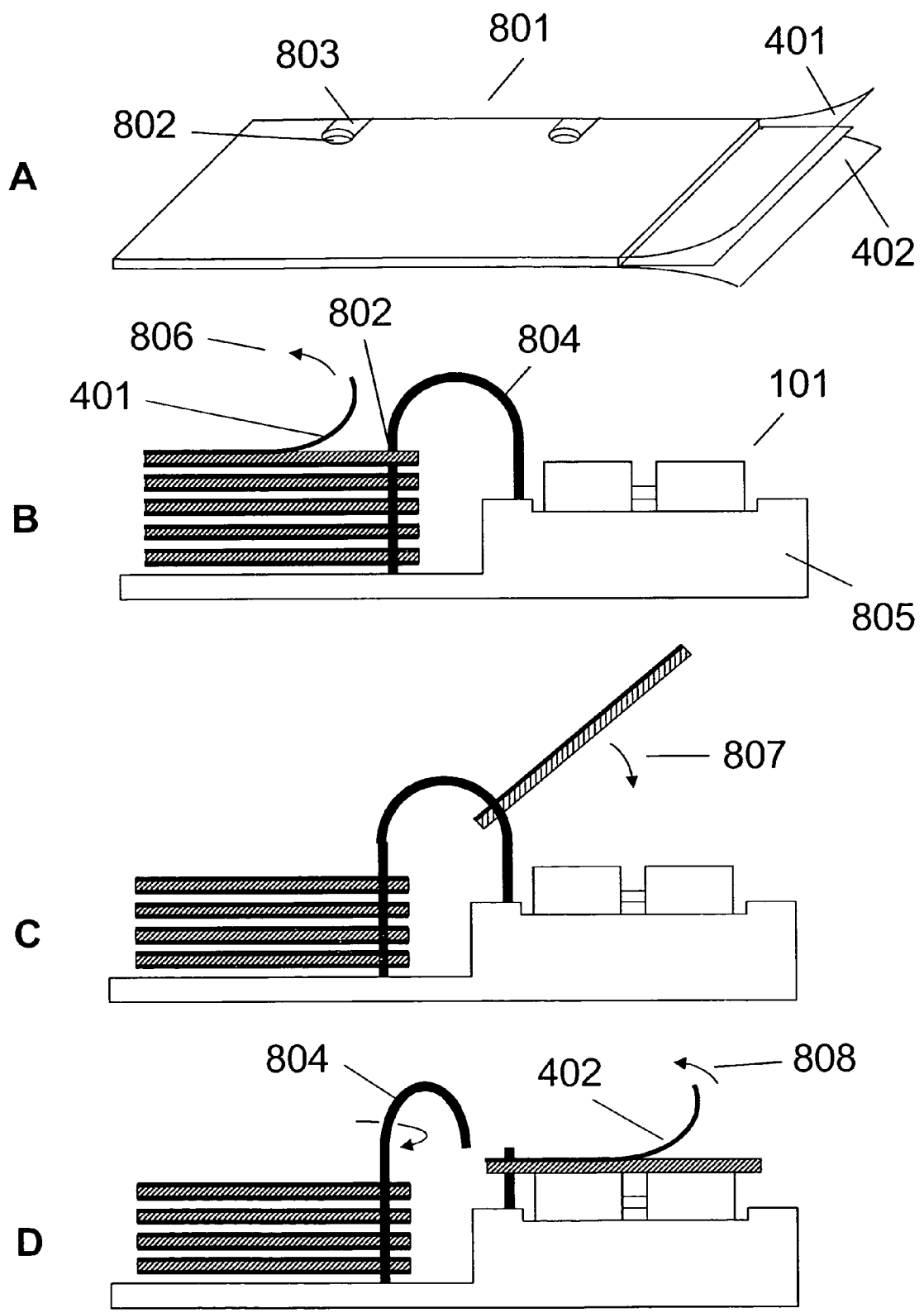
FIGS. 8A through 8D discloses a tray holding a number of interfaces and provides also positioning and placement support mechanism.

Reference is made now to FIG. 8 describing a storage device for multiple interfaces 102 and a mechanism for convenient positioning and mounting of interface 102 onto SVS array 101. Interface assembly 801 shown in FIG. 8A is generally the same as the one of FIG. 4B with the addition of two holes 802 and two cut-offs 803 in liner 401, to enable removal of liner 401 while a ∩-shaped guide 804 (FIG. 8B) is in hole 802.

FIG. 8B presents five interfaces stored on the left side of storage device 805. The length of interface 102 is perpendicular to the plane of FIG. 8. Two guides 804 go through the two holes 802 of the interfaces, holding them in place one on top of the other. On the right hand side of storage device 805 a SVS array 101 is positioned, in registration, by design, to guides 804.

To mount the top-most interface on SVS array 101 the user first peels-off liner 401 as shown by arrow 806. It is appreciated that arrow 806 does not represent the actual direction of peeling liner 401 but is only used to illustrate the concept of peeling. In the next step, illustrated in FIG. 8C, the user flips over the interface by rotating it clockwise, as shown by arrow 807 until the interface rests upon the SVS array surface. Holes 802 in the interface, guides 804 and registration of SVS array to the guides ensure that the interface is positioned with proper registration on the surface of the SVS array. The interface is now pressed by the user onto the surface of the SVS array to ensure proper adhesion.

In the next step, described in reference to FIG. 8D, guides 804 are rotated to clear the way for removal of the interface and SVS array assembly. Liner 402 is removed as shown by illustrative arrow 808 and the assembly is ready for handling for attachment to exposed back 103.

It would be appreciated that the storage device can be used with a specially designed cover to protect the interfaces from dust and dirt. Also, the storage device can be made out of low cost materials such as cardboard and different polymers to reduce its cost to a level it can also be used as the packaging of a set of interfaces, for a single use for this set, being disposable after the interfaces set is exhausted.

It would also be appreciated that the device of FIG. 8 can also be reduced for positioning function only of interfaces onto SVS array by removing the storage part on the left side of the device and replacing guide 804 by straight vertical pins located in registration to the SVS array. The alignment of the interface to the SVS array is made then by first placing the array in the device, then removing liner 401 from an interface and then placing the interface, exposed glue side to the SVS array, with the holes 802 on the pins to get the desired registration to the SVS array.

Figure 9:
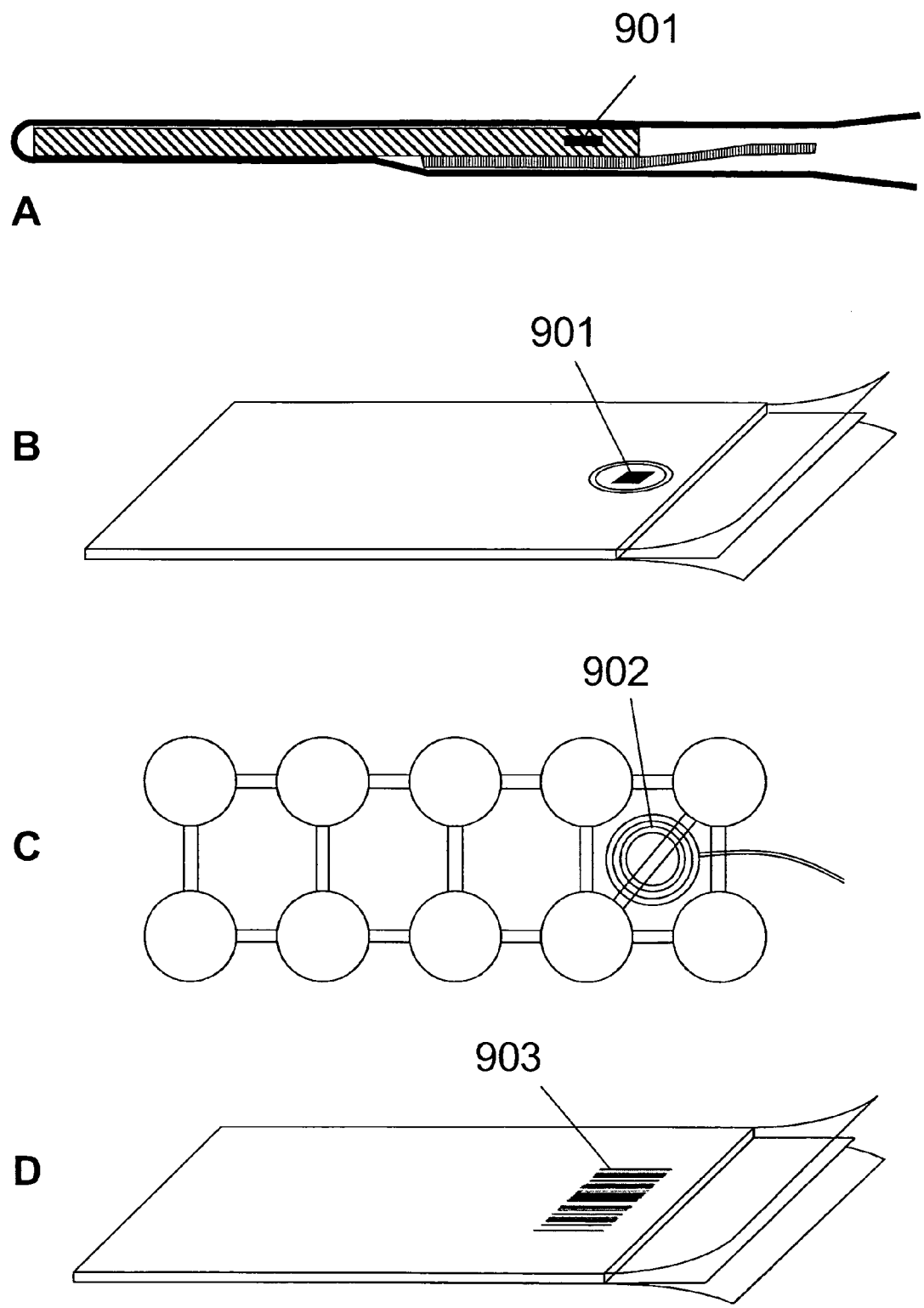
FIGS. 9A through 9D discloses an additional embodiment of the interface of the present invention where RFID or barcode are incorporated to prevent re-use of the interface to avoid cross-contamination potential of multiple uses of the interface.

Reference is made now to FIG. 9, describing another embodiment of the invention where RFID (Radio Frequency Identification) or barcode are used to reduce the risk of cross contamination between patients by ensuring a single use of each interface.

FIG. 9A illustrates generally the same interface assembly as in FIG. 5A, with an added RFID tag 901. Many RFID tags are available in the market, one example is 125 KHz CD20 Unique, part number 601116 manufactured by Cyntag, Inc., Cynthiana, Ky., USA. Also RFID tag reader/writers are widely available, one such example is 125 KHz Q5 RFID Reader/Writer also manufactured by Cyntag, Inc., Cynthiana, Ky., USA. In one embodiment of the invention, the RFID tag is installed in the interface assembly while the antenna 902 of the RFID read/write module is installed in SVS array 101 as shown in FIG. 9C. The RFID reader/writer is not shown in the drawing.

When the interface is mounted in the SVS array, the RFID tag 901 is positioned near the RFID antenna 902. The reader then reads the RFID tag and transfers the data to the computer of the VRIxp (not shown in the drawing). The computer verifies the tag has not been used before. If the data of the RFID tag indicates previous usage, the computer system declines the process with a proper message to the user such as "acquisition cannot be started: the interface has been used with another patient. Please replace interface and try again".

If, however, the data indicates an unused interface, the computer instructs the RFID read/write module to change the data in the tag to indicate "used status" and the acquisition process continues.

It would be appreciated by those skilled in the art that this contamination barrier method using RFID can be implemented in additional ways. For example, each RFID tag may carry an ID number. A given VRIxp machine would accumulate an ID list of all interfaces used in this machine. For each new interface the computer will check if the ID number of this interface is in the used-list or not. If it is, it will decline the continuation of the acquisition process. If it is not in the list, the acquisition with this interface will be allowed.

In yet another implementation of the RFID system of FIGS. 9A and 9B, and the barcode 903 of FIG. 9D, the reading/writing of the information of the RFID tag or the barcode may be disassociated from SVS array 101. In this embodiment the readers are separate from the SVS array and the communication with the RFID tag or the barcode is typically made before attaching the interface to the SVS array.

It would appreciated that the barcode method may include the method mentioned above of generating a list of used interfaces and comparing each new interface to this list by the VRIxp computer. It is also possible to preload the VRIxp with a pre-set ID list of allowed interfaces, for example, by using a "package barcode" mounted on a package of a set of interfaces. This barcode provides the VRIxp with a code enabling the VRIxp software to properly generate the ID list of the interfaces included in this package. Now, when using an interface, the computer will check if the barcode of the interface matches one of the allowed list. If it does, the relevant ID will be marked "used" to disable additional usage of an interface with the same number.

It would be appreciated that the locations of the RFID tags (embedded in the interface bulk) and barcode as shown in FIG. 9 are presented as examples and the invention is not limited to the specific examples.

Figure 10:
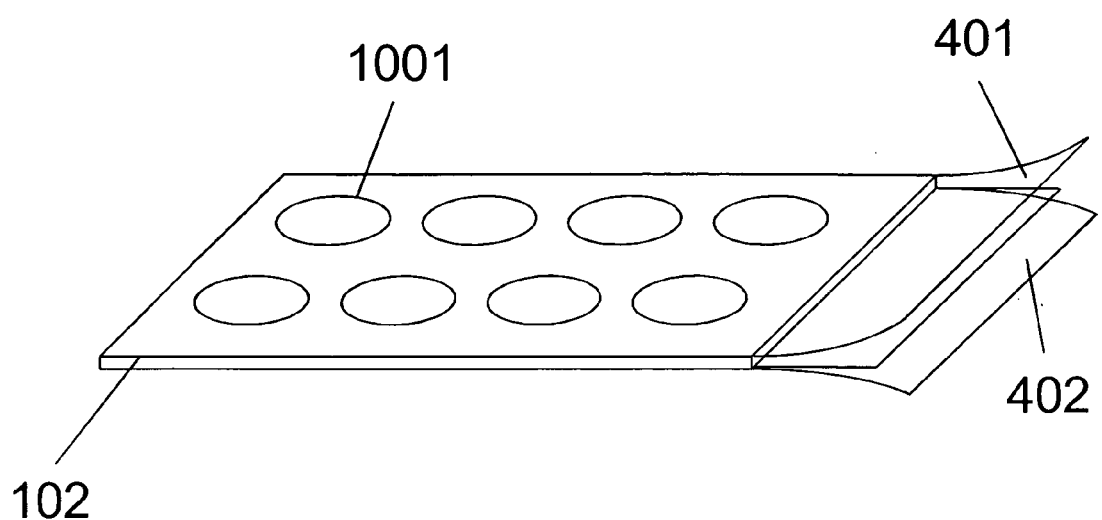
FIG. 10 discloses an additional embodiment of the interface of the present invention, including positioning marks.

Reference is made now to FIG. 10 illustrating positioning marks to help the user register the interface onto the SVS array.

In this example interface 102 and liners 401 and 402 are transparent. Circles 1001 are printed on top of liner 402, these circles having the same geometry as the SVS in the SVS array 101. After the user removes liner 401, he brings the interface in close distance to SVS array 101 and visually aligns the printed circles with the SVS array visible through the interface transparent layers. Once the printed circles and the SVS array geometry are aligned, the user brings the interface and the SVS array into contact and presses the surface of the interface to ensure adhesion to the SVS array. Then liner 402 can be removed for mounting the assembly on exposed back 103.

It would appreciated that the printing geometry is provided here only as an example and other alignment geometries and substrates (such as interface 102 itself) are available.

Figure 11:
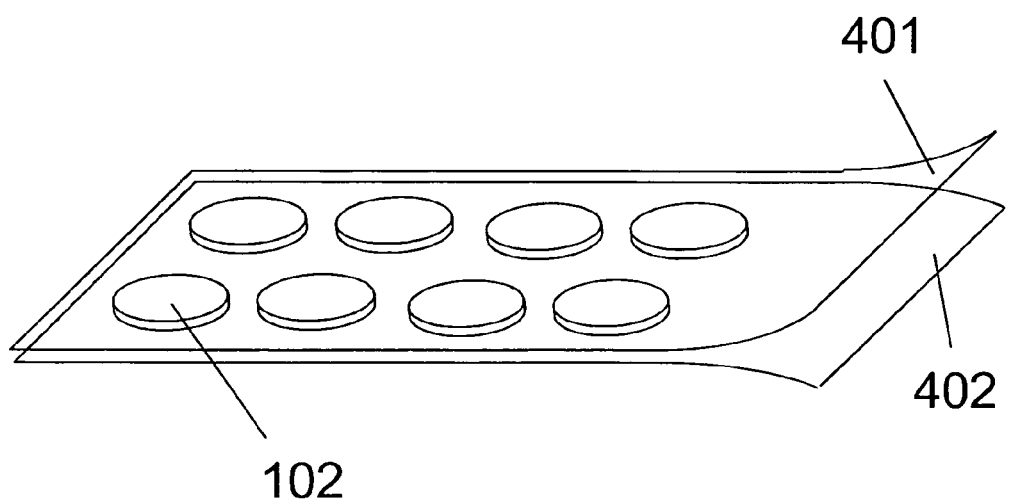
FIG. 11 discloses an additional embodiment of the interface of the present invention, wherein each SVS receives a separate interface.

Reference is made now to FIG. 11 illustrating an interface cut in the shape of isolated circles. With this embodiment, only the interface area that actually binds the SVS to the exposed back 103 is included in the assembly. This method might be more convenient to sensitive skin patients when removing the assembly from their back, after respiratory data acquisition is completed.

In yet another embodiment of the invention, a consideration of children being more sensitive to pulling-off the interface from their skin is made to modify the glue placed on the surfaces of interface 102. In such a case, the side of the interface that contacts the skin of the children is coated with glue with lower adhesive force than the side of the interface facing the SVS array. With this arrangement, pulling off the interface from a child's skin results in a lower irritation force due to the adjusted glue.

The hereinabove embodiments are described in a way of example only and do not specify a limited the scope of the invention.

The invention claimed is:

1. An interfacing assembly for interfacing an array of sound vibration sensors (SVS) to a sound generation object (SGO) comprising:
   a viscoelastic sheet;
   a flexible adhesive coating on each side of said viscoelastic sheet;
   means for attaching said sheet on one side thereof to said array of SVS and on the other side thereof to said SGO, wherein said means for attaching comprise a liner on each side of said sheet; and
   at least one separator between part of said sheet and said liner, for facilitating the peeling of said liner from said sheet.

2. The assembly of claim 1, wherein said at least one separator comprises two separators, each on a respective side of said sheet.

3. The assembly of claim 1, wherein said part of said sheet is clear of glue.

4. The assembly of claim 1 wherein said part of the sheet is coated with non-sticking material.

5. A device for positioning at least one interface assembly for interfacing an array of sound vibration sensors (SVS) to a sound generation object (SGO), comprising pins assembled in registration to an SVS array bed and holes in the at least one interface assembly in conjunction with said pins, such that placing the interface device on the pins registers the interface device to the SVS array which is in the SVS array bed; and
   a tray for holding the at least one interface assembly and guides to help guiding each said at least one interface assembly to the SVS array in proper registration.

* * * * *